(12) United States Patent
Ravikumar

(10) Patent No.: US 9,220,872 B2
(45) Date of Patent: Dec. 29, 2015

(54) BIDIRECTIONAL VASCULAR INTRODUCER SHEATH

(76) Inventor: Sundaram Ravikumar, Briar Cliff Manor, NY (US)

(*) Notice: Subject to any disclaimer, the term of this patent is extended or adjusted under 35 U.S.C. 154(b) by 146 days.

(21) Appl. No.: 13/084,695

(22) Filed: Apr. 12, 2011

(65) Prior Publication Data

US 2012/0010563 A1  Jan. 12, 2012

Related U.S. Application Data

(60) Provisional application No. 61/342,367, filed on Apr. 13, 2010.

(51) Int. Cl.
| | |
|---|---|
| *A61M 25/06* | (2006.01) |
| *A61B 17/34* | (2006.01) |
| *A61M 25/02* | (2006.01) |
| *A61B 17/22* | (2006.01) |
| *A61M 25/09* | (2006.01) |
| *A61M 29/00* | (2006.01) |

(52) U.S. Cl.
CPC ........ *A61M 25/0662* (2013.01); *A61B 17/3415* (2013.01); *A61M 25/02* (2013.01); *A61B 2017/22038* (2013.01); *A61B 2017/3449* (2013.01); *A61B 2017/3486* (2013.01); *A61B 2017/3492* (2013.01); *A61M 25/09041* (2013.01); *A61M 29/00* (2013.01); *A61M 2025/0233* (2013.01)

(58) Field of Classification Search
CPC ............... A61B 17/3423; A61B 2017/3484; A61B 2017/3486; A61B 2017/3488; A61B 17/0057; A61B 2017/22038; A61B 2017/3449; A61B 2017/3492; A61M 2025/0233; A61M 2029/025; A61M 2039/0264; A61M 2039/0258; A61M 2039/0261; A61M 25/04; A61M 39/0247; A61M 25/0662; A61M 2025/0213; A61M 25/09041; A61M 2025/09125
USPC ............ 604/96.01, 912, 915, 102.01–102.03, 604/103.03, 192–194, 284
See application file for complete search history.

(56) References Cited

U.S. PATENT DOCUMENTS

| 5,425,708 | A | * | 6/1995 | Nasu ......................... 604/102.03 |
|---|---|---|---|---|
| 5,599,329 | A | * | 2/1997 | Gabbay .......................... 604/284 |
| 6,099,506 | A | * | 8/2000 | Macoviak et al. ............. 604/173 |
| 2002/0128597 | A1 | * | 9/2002 | Grimes et al. ............. 604/96.01 |
| 2004/0015151 | A1 | * | 1/2004 | Chambers ..................... 604/532 |

* cited by examiner

*Primary Examiner* — Nicholas Lucchesi
*Assistant Examiner* — Morgan Lee
(74) *Attorney, Agent, or Firm* — Theresa O'Rourke Nugent; Nugent + Smith, LLP

(57) ABSTRACT

A vascular introducer sheath includes a sheath body having an interior lumen for accommodating a dilator. The vascular introducer further includes a guidewire positioning means operatively associated with the interior lumen of the sheath body for directing a guidewire in either a vascular direction or an arterial direction within a venous system.

5 Claims, 5 Drawing Sheets

BIDIRECTIONAL VASCULAR INTRODUCER SHEATH

CROSS-REFERENCE TO RELATED APPLICATIONS

This application claims benefit of priority from U.S. Provisional Patent Application No. 61/342,367 filed Apr. 13, 2010, which is incorporated by reference herein in its entirety.

BACKGROUND OF THE INVENTION

1. Field of the Invention

The subject invention is directed generally to a vascular introducer sheath, and more particularly, to a vascular introducer sheath that is adapted and configured to facilitate bi-directional access to the venous system.

2. Background of the Related Art

Vascular introducers are well know in the art and have been employed for inserting catheters, guidewires and the like into patients. A typical procedure provides for insertion of a dilator or needle within a sheath into the vasculature of a patient. After insertion, the dilator may be removed leaving the sheath protruding from the patient's vein. A diagnostic or therapeutic catheter (e.g. a central venous access catheter) or guide wire is then inserted through the sheath into the patient. The sheath is then typically longitudinally sheared and removed from the catheter or guidewire and the patient such as by applying opposing force to opposed wings or tabs of the introducer device. See for example U.S. Pat. No. 5,741,233 to Riddle et al. which is incorporated by reference in its entirety.

In prior art vascular introducers, the sheath permits uni-directional introduction of a guidewire into the venous system. This prevents the sheath from going to the opposite side of the vessel to conduct any procedures. If the opposite side of the vessel needs to be accessed, it requires another separate entry in the artery vessel. It would be beneficial however to provide an introducer sheath that is adapted and configured to facilitate bi-directional introduction of a guidewire into the venous system, i.e., in either a vascular or an arterial direction.

SUMMARY OF THE INVENTION

The subject invention is directed to a bi-directional vascular introducer sheath that includes a sheath body having an interior lumen for accommodating a dilator and a J-shaped guidewire positioning device. The guidewire positioning device is operatively associated with the interior lumen of the sheath body and is adapted and configured to direct a guidewire in either a vascular direction or an arterial direction within the venous system.

In one embodiment of the subject invention, a distal portion of the sheath body has a J-shaped configuration and an aperture is formed in the distal portion of the sheath body at a joint of the J-shaped configuration to facilitate bi-directional positioning of a guidewire using the J-shaped guidewire positioning device.

In another embodiment of the subject invention, a distal portion of the sheath body is longitudinally split and is adapted to move between a naturally spread open position and a longitudinally closed position. Preferably, a movable ring maintains the split distal portion of the sheath body in the closed position. Once the split sheath has spread to an open position, the J-shaped guidewire positioning device facilitates bi-directional positioning of a guidewire. Alternatively or in addition to using the movable ring to facilitate spreading of the split distal portion of the sheath body, it is envisioned that a distal portion of the sheath body may be made from a material which moves to a preset spread open condition upon exposure to body temperature. In this regard, it is envisioned that at least a distal portion of the sheath body may be made from a shape memory alloy.

These and other aspects of the vascular introducer sheath of the subject invention will become more readily apparent from the following description taken in conjunction with the drawings.

BRIEF DESCRIPTION OF THE DRAWINGS

So that those having ordinary skill in the art to which the subject invention pertains will more readily understand how to make and use the female connector of the subject invention, preferred embodiments thereof will be described in detail hereinbelow with reference to the drawings, wherein:

FIG. 4 shows the proximal movement of the support ring shown in FIG. 3 during vascular introduction;

DETAILED DESCRIPTION OF THE PREFERRED EMBODIMENTS

Figure 1:
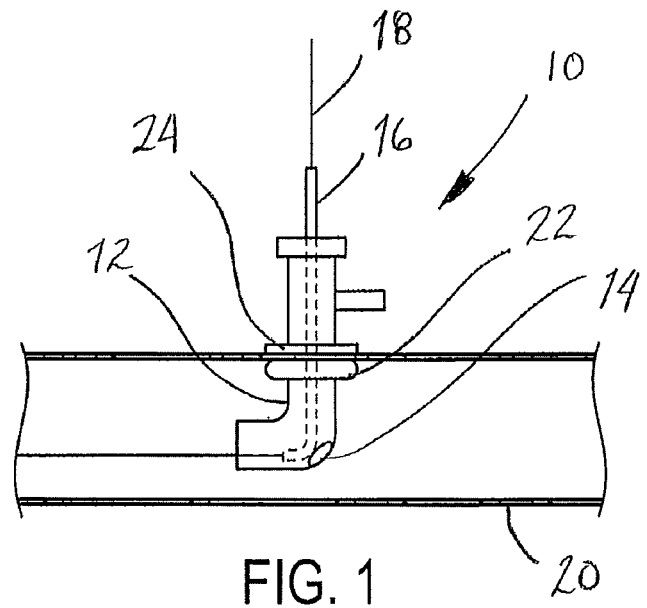
FIG. 1 is an illustration of a vascular introducer configured in accordance with a preferred embodiment of the subject invention which includes a J-shaped bi-directional introducer sheath having a side port, and adapted to accommodate a guidewire positioning device which is oriented in a first direction.
Figure 2:
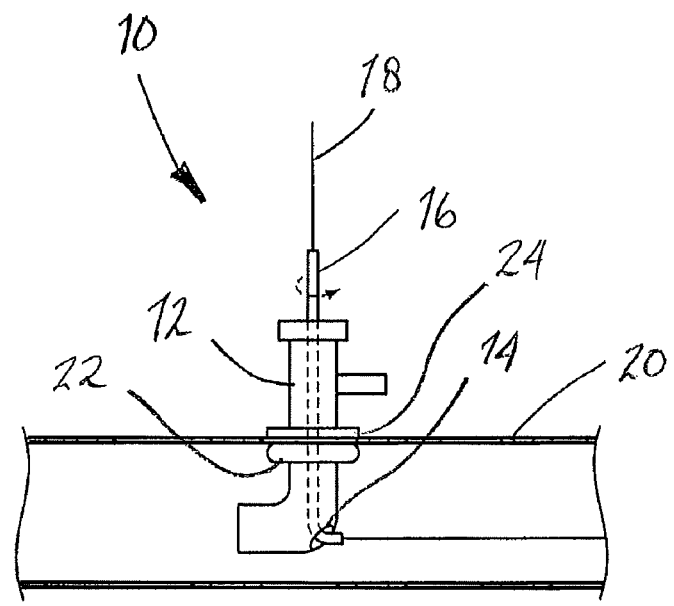
FIG. 2 shows the guidewire positioning device of FIG. 1 oriented in a second direction relative to the introducer sheath.

Referring now to the drawings wherein like reference numeral identify similar structural features of the vascular introducer sheath of the subject invention, there is illustrated in FIG. 1 a vascular introducer 10 configured in accordance with a preferred embodiment of the subject invention. Introducer sheath 10 includes a generally J-shaped bi-directional sheath 12 having a side port 14 located at the joint of the J-shaped sheath. Sheath 12 is adapted and configured to accommodate a rigid J-shaped tubular guidewire positioning device 16. In a first orientation, the guidewire positioning device 16 directs a guidewire 18 out the distal end of the sheath in a first direction into a blood vessel 20. As shown in FIG. 2, when the guidewire positioning device 16 is rotated or otherwise oriented in a second position, the guidewire 18 is directed out the side port 14 in a second opposite direction within blood vessel 20. Introducer sheath 12 also includes a balloon anchor 22 associated with the inner vessel wall and an annular disk anchor 24 associated with an outer vessel wall or the skin for sealing and anchoring.

Figure 3:
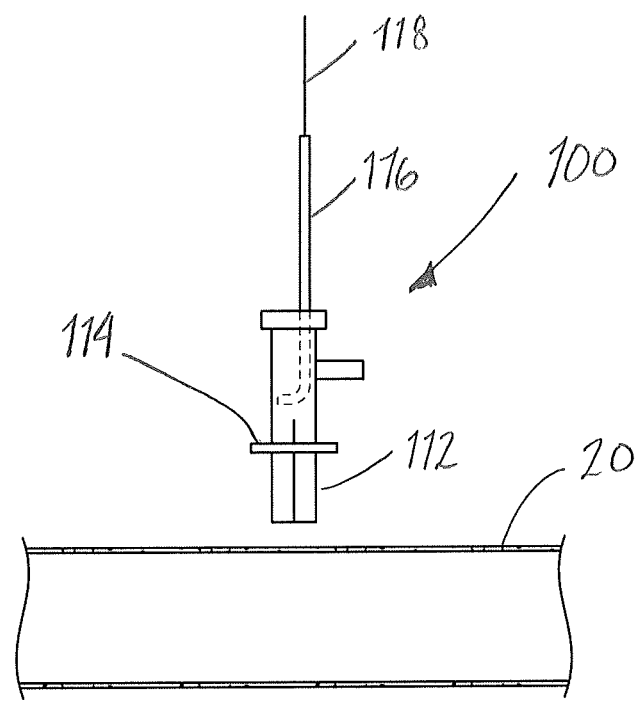
FIG. 3 is an illustration of another embodiment of the bi-directional vascular introducer sheath of the subject invention, wherein the distal section of the sheath is split and is initially held together by a movable support ring during vascular introduction.
Figure 5:
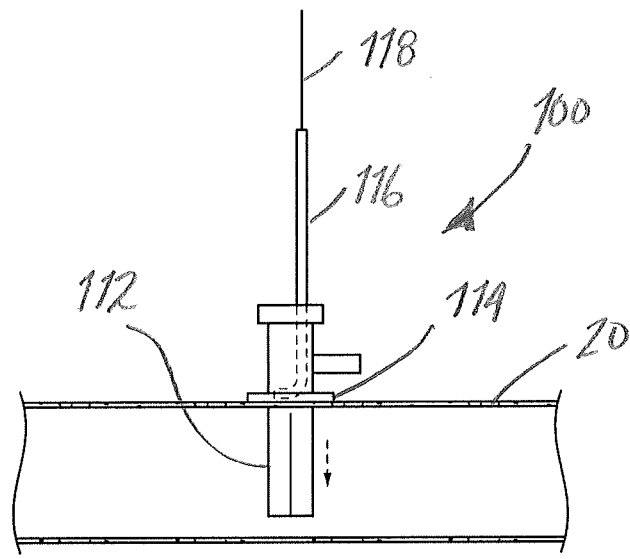
FIG. 5 shows the split sheath of FIG. 3 prior to spreading into an open position in the blood vessel.
Figure 6:
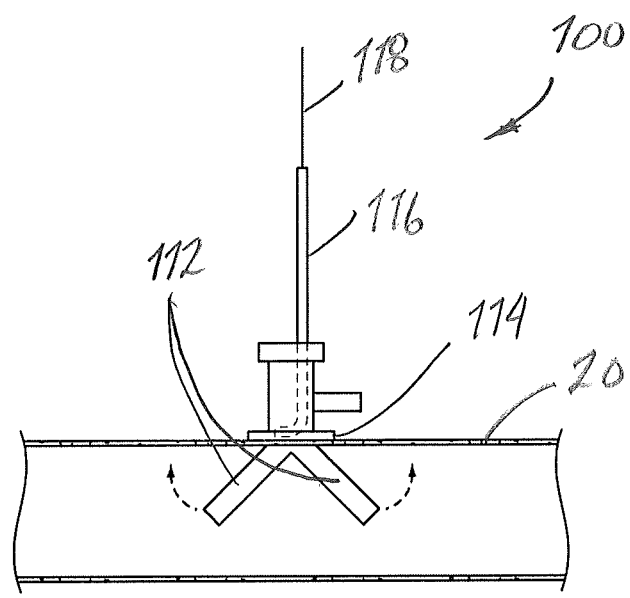
FIG. 6. illustrates the split vascular sheath of FIG. 3 spreading into an open position within a blood vessel.
Figure 7:
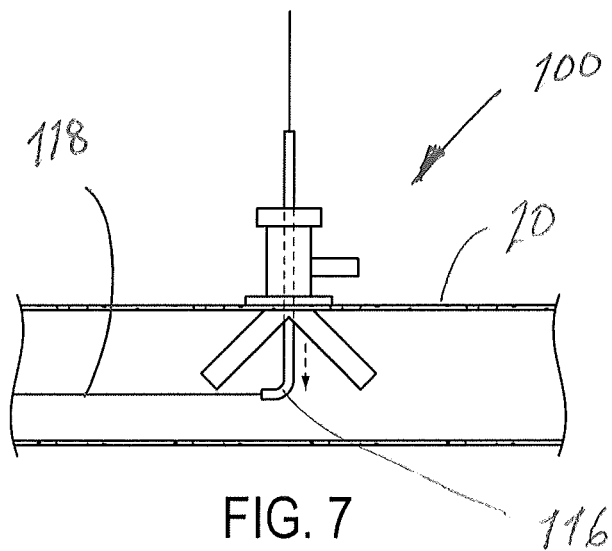
FIG. 7 illustrates the split vascular sheath of FIG. 6 with the guidewire positioning device oriented in a first direction.
Figure 8:
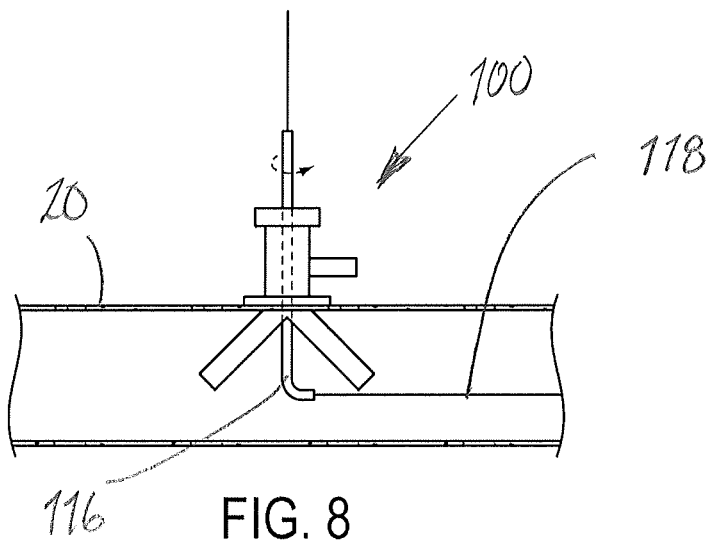
FIG. 8 illustrates the split vascular sheath of FIG. 6 with the guidewire positioning device oriented in a second direction.

Referring now to FIG. 3, there is illustrated another embodiment of a bi-directional vascular introducer sheath of the subject invention, which is designated generally by reference numeral 100. Sheath 100 has a distal section 112 that is longitudinally split along diametrically opposed cut-lines and is initially held together by a movable support ring 114 during vascular introduction. As shown in FIGS. 4 through 6, the split distal section 112 of sheath 100 is spread into an open position as the support ring 114 is moved proximally during introduction of the sheath into a blood vessel 20. Once spread into an open position, the split distal section 112 of sheath 100 anchors the sheath against the inner wall of the blood vessel, preferably in conjunction with the support ring 114 positioned with respect to the outer wall of the blood vessel. It is also contemplated that, when the split distal section 112 of sheath 100 is spread into an open position, the split distal section 112 may be opened flush with the wall of the artery. In use, as shown in FIGS. 7 and 8, a J-shaped guidewire positioning device 116 may be oriented within the interior lumen of split sheath 112 in first and second opposite directions to direct a guidewire 118 into the venous system in first and second opposite directions.

Alternatively or in addition to using the movable support ring 114 to facilitate spreading of the split distal section 112 of the sheath 100 into an anchoring position within blood vessel 20, it is envisioned that the distal section 112 of sheath 100 may be made from a material which moves to the preset spread open condition upon exposure to body temperature. In this regard, it is envisioned that at least the distal portion 112 of the sheath 100 may be made from a shape memory alloy.

Figure 9:
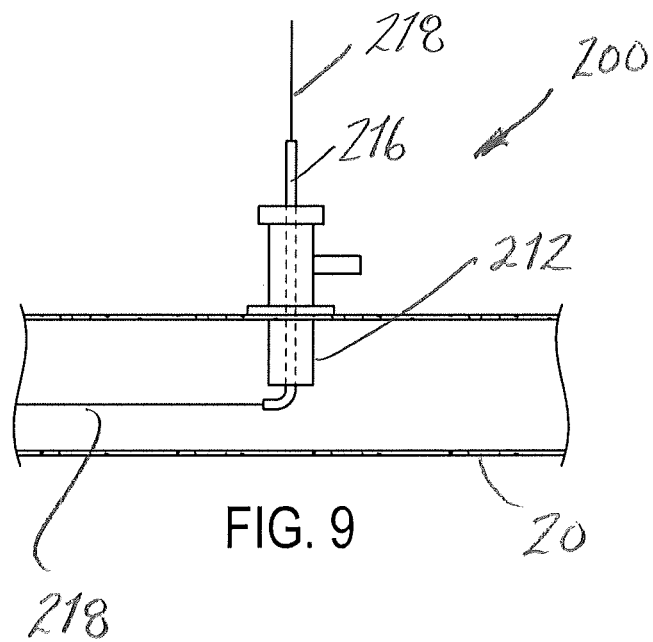
FIGS. 9 and 10 illustrate yet another embodiment of the bi-directional introducer sheath of the subject invention, wherein the sheath is dimensioned and configured to accommodate the guidewire positioning device in first and second opposite directions.
Figure 10:
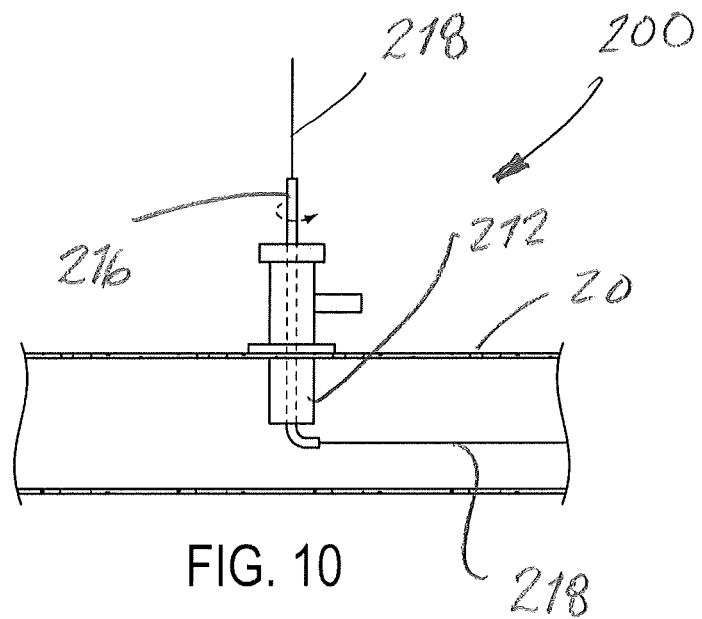

Referring now to FIGS. 9-10, there is illustrated yet another embodiment of the bi-directional introducer sheath of the subject invention, which is designated generally by reference numeral 200. Sheath 200 includes an elongated distal portion 212 having an interior lumen that is dimensioned and configured to accommodate a J-shaped guidewire positioning device 216, which is shown oriented in first and second directions to facilitate introduction of a guidewire 218 in opposite directions within a blood vessel 20.

While the subject invention of the present disclosure has been described with respect to preferred and exemplary embodiments, those skilled in the art will readily appreciate that various changes and/or modifications can be made to the invention without departing from the spirit or scope of the invention as described herein.

What is claimed is:

1. A vascular introducer sheath comprising:
a) a sheath body having a j-shaped configuration and defining an interior lumen in communication with an open distal end of the sheath body and an aperture;
b) a rigid J-shaped tubular body operatively associated with the interior lumen of the sheath body configured and adapted to direct a guidewire in either a first direction through the open distal end into a flowing blood vessel or a second opposite direction through the aperture opposite the open distal end into the blood vessel within a venous system wherein the guidewire may be moved in either an arterial or vascular direction; and
c) a sealing and anchoring means for sealing an upper wall of the blood vessel and anchoring a portion of the sheath body just below the upper wall of the blood vessel to the upper wall while not occluding the blood flow within the blood vessel,
wherein the means for sealing and anchoring includes an annular balloon anchor operatively associated with an outward portion of the sheath body above a curved joint portion of the J-shaped tubular body and an annular disk anchor operatively associated with an outward portion of the sheath body mounted latitudinally above the annual balloon anchor such that the annular balloon anchor and annular disk anchor are configured and adapted to anchor the sheath body with respect to an upper wall of the blood vessel.

2. The vascular introducer as recited in claim 1, wherein the aperture is formed in the distal portion of the sheath body at a joint of the J-shaped configuration.

3. The vascular introducer as recited in claim 2, wherein the aperture is sized to allow movement of the rigid J-shaped tubular body therethrough.

4. The vascular introducer as recited in claim 1, wherein the annular balloon is configured and adapted to anchor the sheath body with respect to an interior wall of the blood vessel while allowing passage of the guidewire in either of the first and second directions.

5. The vascular introducer as recited in claim 1, wherein the sheath body has a J-shaped configuration which includes a first portion configured and adapted to extend transversely through a wall of the blood vessel and a second portion configured and adapted to be oriented substantially parallel to the blood vessel, and wherein the annular balloon is operatively disposed circumferentially about the first portion.

* * * * *